US006688564B2

(12) United States Patent
Salvermoser et al.

(10) Patent No.: US 6,688,564 B2
(45) Date of Patent: Feb. 10, 2004

(54) FLEXIBLE TENSIONING DEVICE, ESPECIALLY FOR MEDICAL PURPOSES

(75) Inventors: Markus Salvermoser, Tuttlingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 10/273,940

(22) Filed: Oct. 18, 2002

(65) Prior Publication Data

US 2003/0089831 A1 May 15, 2003

Related U.S. Application Data

(63) Continuation of application No. PCT/EP01/03883, filed on Apr. 5, 2001.

(30) Foreign Application Priority Data

Apr. 19, 2000 (DE) ........................................ 100 19 321

(51) Int. Cl.[7] ................................................ F16M 13/00

(52) U.S. Cl. .................... 248/160; 248/288.31; 403/56; 403/143

(58) Field of Search .............................. 248/160, 276.1, 248/288.31, 288.51, 104, 481, 484, 663; 403/56, 90, 122, 127, 141–143

(56) References Cited

U.S. PATENT DOCUMENTS

| | | | | |
|---|---|---|---|---|
| 354,976 A | | 12/1886 | Field | |
| 816,240 A | | 3/1906 | Mehlig | |
| 897,349 A | | 9/1908 | Coates | |
| 958,052 A | * | 5/1910 | Williams | 403/56 |
| 1,455,411 A | * | 5/1923 | Hodny | 403/56 |
| 1,502,265 A | * | 7/1924 | Paterson | 403/141 |
| 1,528,967 A | | 3/1925 | Bersted | |
| 1,947,965 A | | 2/1934 | Beggs | 64/91 |
| 2,526,045 A | * | 10/1950 | Riemann | 403/56 |
| 2,533,494 A | * | 12/1950 | Mitchell, Jr. | 403/56 |
| 2,752,726 A | | 7/1956 | Calverley | 46/22 |
| 3,278,207 A | | 10/1966 | Barish et al. | 287/12 |
| 3,490,798 A | * | 1/1970 | Spyra | 403/56 |
| 3,825,356 A | * | 7/1974 | Crook, Jr. | 403/122 |
| 3,858,578 A | | 1/1975 | Milo | 128/20 |
| 4,044,725 A | * | 8/1977 | Miller | 403/122 |
| 4,141,225 A | * | 2/1979 | Varner | 403/353 |
| 4,382,572 A | | 5/1983 | Thompson | 248/484 |
| 4,491,435 A | | 1/1985 | Meier | 403/55 |
| 4,606,522 A | | 8/1986 | Heifetz | 248/276 |
| 4,648,733 A | * | 3/1987 | Merkt | 403/56 |
| 4,898,490 A | | 2/1990 | Herbermann et al. | 403/56 |
| 5,046,764 A | * | 9/1991 | Kimura et al. | 403/56 |

FOREIGN PATENT DOCUMENTS

| | | |
|---|---|---|
| CH | 437 461 | 11/1967 |
| DE | 691 06 701 | 7/1995 |
| DE | 297 20 250 | 3/1998 |
| FR | 881 607 | 4/1943 |

* cited by examiner

*Primary Examiner*—Korie Chan
(74) *Attorney, Agent, or Firm*—St. Onge Steward Johnston & Reens LLC

(57) ABSTRACT

The invention comprises a flexible tightening device, especially for medical purposes, with one of several jointed element pivotable against one another existing arm, in which the arm can be locked into the desired position of the locking element by means of a tightening element. In order to create a simply constructed tightening device, which is also easy to clean, which can be adjusted on many sides and is lockable, the invention is suggested, in which each jointed element demonstrates a ball joint at one end and at the opposite end a socket joint to receive the ball joint and that each jointed element is constructed in the length direction in two parts, whereby the individual length pieces are adjustable against one another for locking purposes.

8 Claims, 3 Drawing Sheets

1
2
3
4
5
8
9

3
4
5
6
7
8
9
11
2a
2b
α

FLEXIBLE TENSIONING DEVICE, ESPECIALLY FOR MEDICAL PURPOSES

This application is a continuation of pending International Application No. PCT/EP01/03883 filed Apr. 5, 2001, which designates the United States and claims priority from pending German Application No. 10019321 filed Apr. 19, 2000.

FIELD OF THE INVENTION

The invention comprises a flexible tightening device, especially for medical use, with an arm comprising of several jointed elements, which can pivot against each other, in which the arm can be locked in the current present pivotal position of the locking element by means of a tightening element.

Flexible tightening device such as those which are well-known especially in the sphere of medicine, where they serve to secure a medical tool, for example a spatula in a wound opening during an operation. These well-known tightening devices are essentially in the form of spheres and pipes, which are pulled by a flex on the inside. In order to lock the arm in any given position, the cord is tightened, whereby a friction stop is created between the sphere and the pipes, which stiffens the arm in the installed position. A disadvantage of this flexible tightening device is that because of the cord running through the interior the cavities and the cord are almost impossible to clean.

One generic tightening device is known as the U.S. Pat. No. 897,349. With this known tightening device the individual jointed elements are constructed in three parts in the direction of the length and demonstrate at one end a ball joint and at the opposite end a socket joint to receive a ball joint. Both socket joint forming length pieces of each jointed element can be fastened to each other by two the length pieces penetrating bolts, whereby at the same time a shaft bearing the ball joint inside each length piece of a joint element may be fastened by means of bolts. Each jointed element of this known tightening device consists of three components, namely the two length pieces and the shaft bearing the ball joint. Very precise production techniques are required with little margin for error, since in the assembly of the jointed elements, it is of the utmost importance that the bores in both length pieces and in the shaft are in exact alignment with each other, so that these components can be connected to one another by means of bolts. Therefore, on the one hand, the individual jointed elements of this tightening device can only be manufactured exactly at great expense and on the other expensive manual work is required, in order to fit together the individual components of each jointed element. This therefore makes the production costs for such a well-known tightening device very high.

Starting from this position, the idea behind this invention was to create a flexible tightening device of the type named above, which on one side may be adjusted and locked on more than one side and is also simple to construct, in order to enable simple assembly and complete cleaning.

The solution to this task is supplied by the invention which is characterized by the fact that each jointed element demonstrates at one end a ball joint and at the opposite end a socket joint to receive a ball joint. In addition, each jointed element is constructed in two parts in its length element, whereby the individual length pieces are adjustable with each other for locking purposes.

By using the invention's ball and socket joint links to connect the individual jointed elements it is possible to adjust the arms of the invention that can be tightened with as much freedom as possible. Furthermore it is possible to lock the arm in any of these positions simply, so that the shape of the ball joint is made through adjustment of the length pieces of each of the jointed element in relation to one another. The simple two-part construction of the jointed element without interior components and other cavities further eases the assembly and cleaning of the invention's flexible tightening device.

In accordance with a favoured working form the invention is suggested, that the length pieces of the locking elements constructed in the length direction are constructed in z-form from the side view that on a length piece, a ball joint is connected to the lower part of the socket joint and with the other length piece of the same jointed element of the lower part of the ball joint with the upper part of the socket joint.

For the opposite side adjustment of the length parts of a jointed element, the jointed element demonstrates a joint axle for both length pieces. These joint pivot axles ensure that on one hand the ball joint piece and the socket joint element of each length piece are adjusted and on the other the adjustment of the length pieces to one another follows in the same way.

The pivotal axis for the length pieces of each jointed elements is constructed in the middle of the jointed element and at the level of the lengthways cut through the ball and socket joint, which are so constructed that the length parts can be pivoted against one another with the result that the ball joint and the socket joint can be expanded to an angle or aperture $\alpha$ between the length parts. Through the opening of the socket joint, the ball joint is automatically expanded so that the same degree is expanded that will lead to an adjustment in the socket joint, in which the ball joint rests. This opposite adjustment leads to the locked position of the flexible arm in the chosen pivotal position.

Furthermore, it is suggested with the invention that the angle of aperture from the proximal jointed element to the distal jointed element from jointed element to joint element is represented by $$\alpha_{prox} > \alpha_n > \alpha_{n+1} > \ldots > \alpha_{dist} \cong 0$$

In order to guide the jointed elements to the opposite adjustment on one hand and on the other to limit the angle of pivot, a through bore is constructed at right angles to the length part of the ball joint through the spherical equator of each jointed elements. In this bore for each length part of the ball joint a protruding pin may be inserted from outside above the outer surface of the ball joint, which in the condition when it is linked with another jointed element is guided in a groove constructed in the socket joint.

For the adjustment and tightening of the flexible arm, a handle forming a tightening element can be locked to the proximal end of the arm forming a jointed element, by which the proximal socket joint is expandable.

Finally, it is suggested with the invention, that at the jointed element the distal element of the arm a tool can be attached.

BRIEF DESCRIPTION OF DRAWINGS

Further points of note and advantage in the invention can be found in the following description of the pertinent design, in which a worked out example of a constructed flexible tightening device as per the invention is portrayed as an exemplar design illustrated in the design.

DETAILED DESCRIPTION OF DRAWINGS

Figure 1:
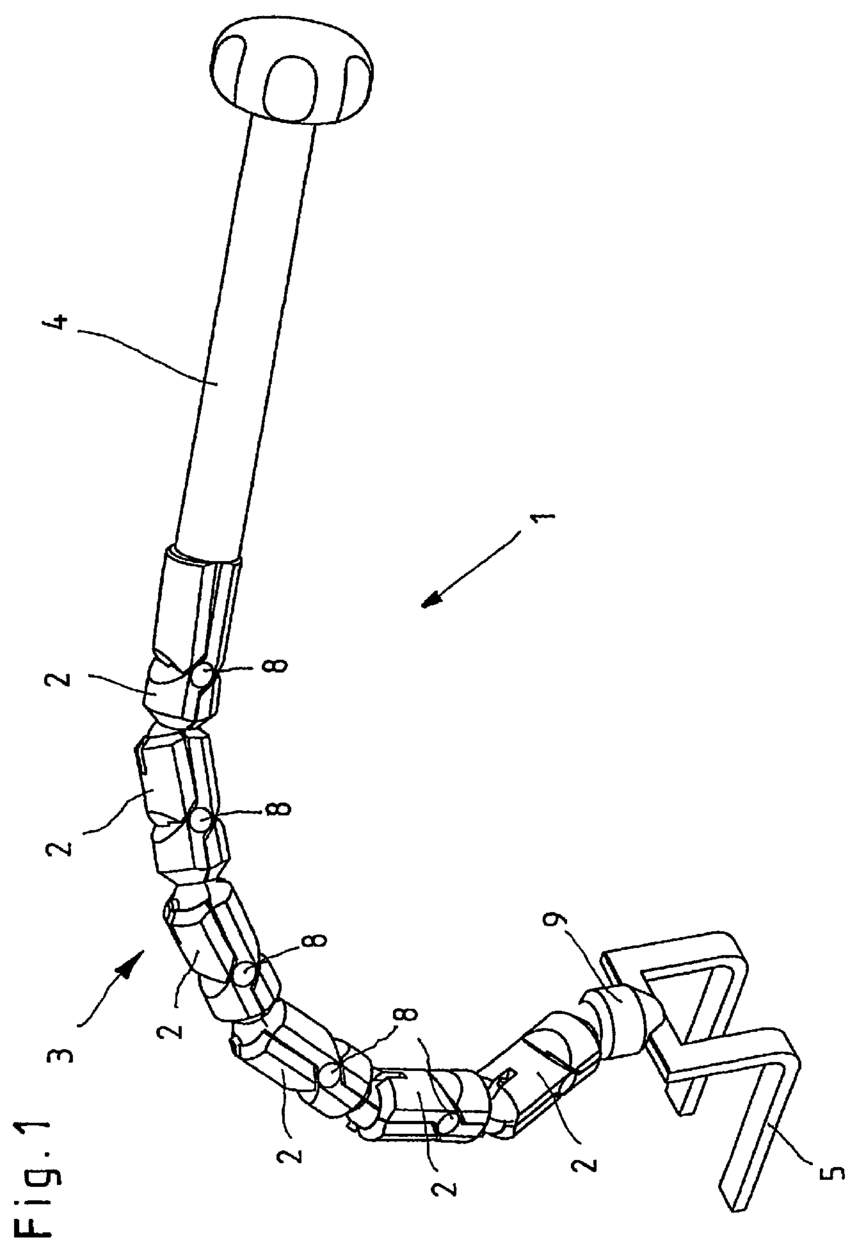
FIG. 1 a side view in perspective of a flexible tightening device as per the invention with proximal handle and distal tool.

The product in FIG. 1 demonstrates a perspective view of a flexible tightening device 1, as it is used especially in medicine, in order for example to hold a tool securely and tightly in one place. The portrayed tightening device 1 essentially comprises an arm 3 made of several jointed elements 2, which can pivot against each other, at the proximal end of which is fixed a handle 4 and at the distal end a tool 5.

Figure 3A:
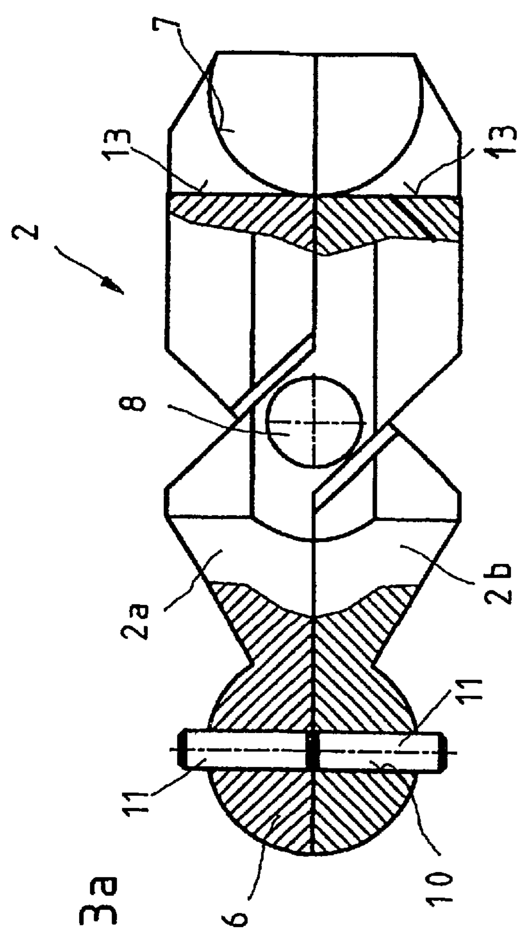
FIG. 3*a* a partly cutaway and enlarged side view of a jointed element.
Figure 3B:
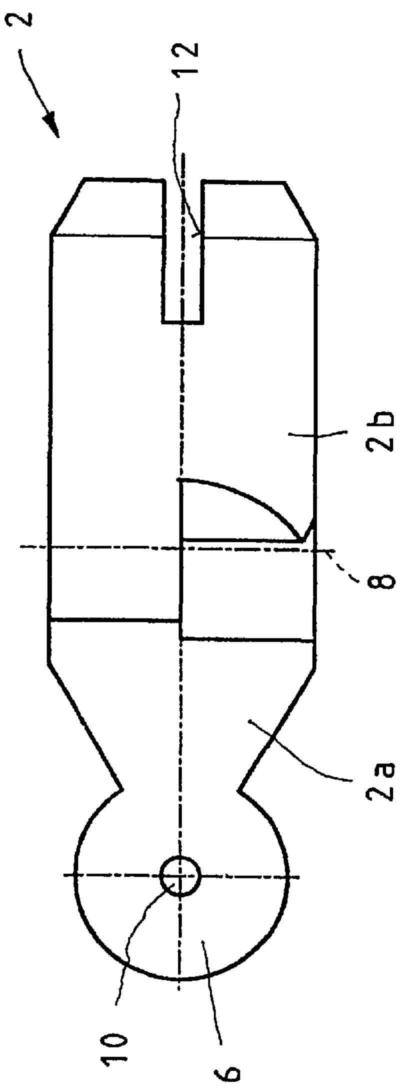
FIG. 3*b* an uncut side view of the jointed element rotated through 90° as in FIG. 3*a*.

As is especially apparent in FIGS. 3*a* and 3*b*, each jointed element 2 demonstrates at one end a ball joint 6 and at the opposite end a socket joint 7 for the reception of a ball joint 6. Through these ball joint connections the flexible arm 3 displays the greatest deal of freedom of movement, so that the arm 3, as shown in FIG. 1, almost rotates at will and can be pivoted likewise.

In order to be able to lock the pivoted arm 3 in any required position and thereby to avoid any further adjustment of the jointed elements 2 against one another, each jointed element 2 is constructed in two parts in the length direction, as shown in FIGS. 3*a* and 3*b*. Both length pieces 2*a* and 2*b* of each jointed element 2 are constructed in the illustrated worked example in the side view as Z shaped, whereby the division is carried out in such a way that with the length piece 2*a* the upper part of the ball joint 6 is connected to the lower part of the socket joint 7 and with the length part 2*b* of its jointed element 2 of the lower part of the ball joint 6 with the upper part of the socket joint 7.

Figure 2:
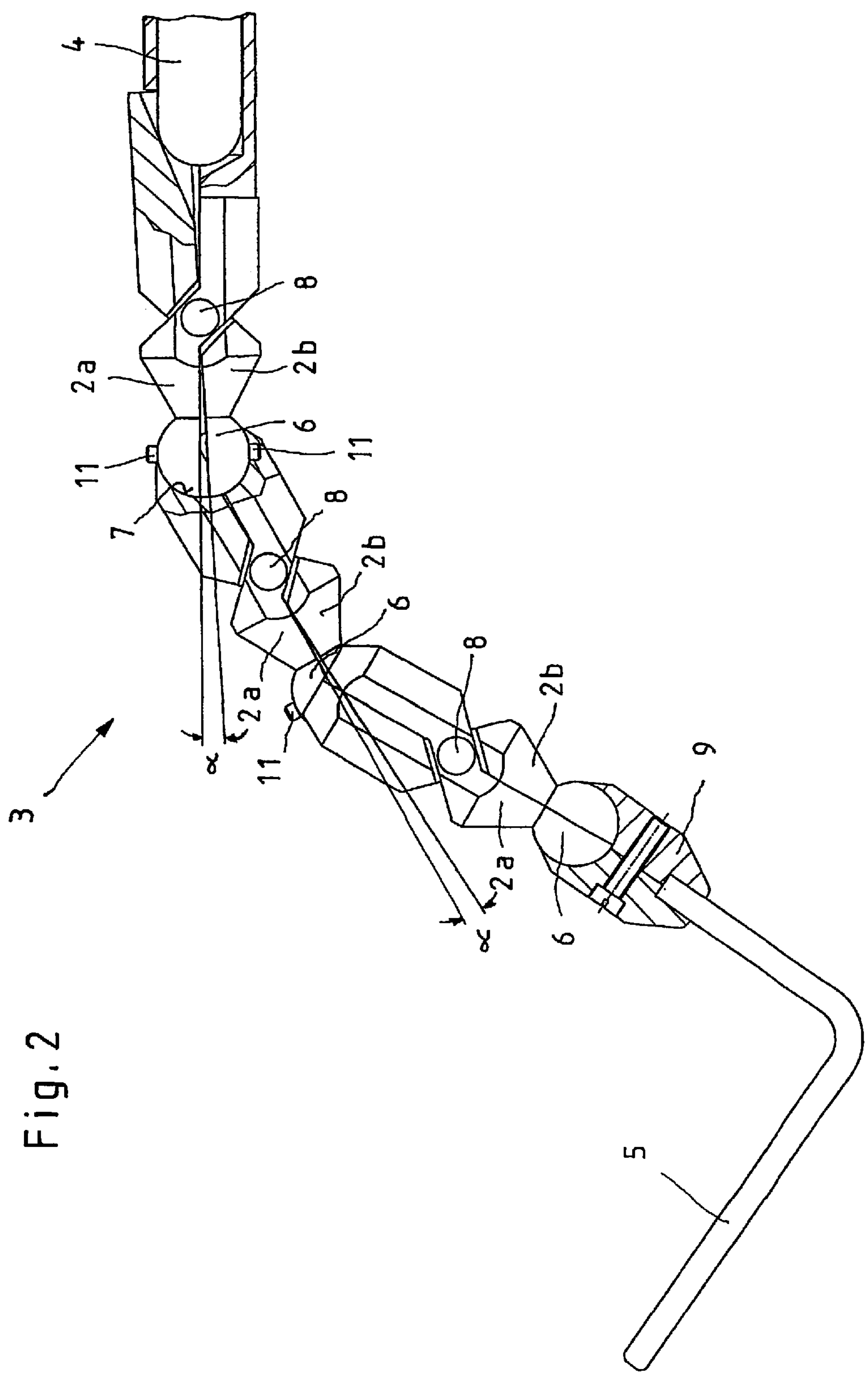
FIG. 2 an enlarged and partly cutaway detailed extract of the product in FIG. 1.

In the transition area between ball joint section 6 and socket joint section 7 each length piece 2*a* and 2*b* is connected to each other by a traversing axle pin 8 at the level of the lengthways cut. This joint axle 8 for both length pieces 2*a* and 2*b* enables such a pivot of the length pieces 2*a*, 2*b* towards one another, that between the parts of the ball joint 6 and the parts of socket joint 7 an angle of aperture is created, as in the exploded diagram in FIG. 2.

Through the opening of the socket joint 7 of a jointed element 2, the ball joint 6 of the same jointed element 2 is opened at the same time, through the axle 8 by which this is adjusted in the socket joint 7 of the following jointed element 2 and opens this socket joint 7. This opposite opening of socket joint 7 and ball joint 6 leads to a complete stiffening of the flexible arm 3, so that this is fixed in place. As seen specifically in FIG. 2, the angle of aperture α from the proximal end of arm 3 to the distal end of the jointed element 2 to the jointed element 2 as follows from $$\alpha_{prox} > \alpha_n > \alpha_{n+1} > \ldots > \alpha_{dist} \cong 0.$$

In the illustrated working example of a tightening device 1, the opening of the socket joint 7 of the proximal jointed element 2 ensues by means of the handle 4 serving as a tightening element. The tool 3 disposed at the distal end of the arm 3 is connected to the ball joint 6 of the distal jointed element 2 by a connecting piece 9.

On one side, the jointed elements 2 at the opposite side movement to lead and on the other to limit the angle of aperture, each ball joint 6 demonstrates at right angles to the length piece a through bore 10 in the area of the sphere's equator. In the through bore 10 of each ball joint part 6 a pin 11 is set up in such a way, that it projects through the outer surface of the sphere of the ball joint 6. In each socket joint 7 there is a corresponding groove 12 to receive the pin 11. The interior walls of the groove 12 serve thereby as stop plates 13 to limit the angle of movement.

A tightening device 1 constructed in this way is characterized by the fact that the arm 3 displaces in directions close to those desired and can be locked in the current position. The simple construction of the individual jointed elements 2 without hidden cavities enables the tightening device 1 to be cleaned easily and completely.

As well as the illustrated opening of ball joint 6 and socket joint 7 it is also possible to target the adjustment of the jointed elements 2, so that the individual length pieces 2*a* and 2*b* of the jointed elements 2 are moved against one another. Because of the division of the jointed elements 2 in at least two length pieces 2*a*, 2*b*, which are adjustable against one another, each distortion of the ball joint 6 effects a jamming in the corresponding socket joint 7 and thereby locks the flexible arm 3.

List of Components

- 1 Tightening device
- 2 Jointed element
- 2*a* Length piece
- 2*b* Length piece
- 3 Arm
- 4 Handle
- 5 Tool
- 6 Ball joint
- 7 Socket joint
- 8 Axle/Axle pin
- 9 Connecting piece
- 10 Through bore
- 11 Pin
- 12 Groove
- 13 Buffer plate
- α Angle of aperture

What is claimed is:

1. A flexible tightening device, having an arm comprising several jointed elements moveable against one another, in which the arm may be locked in a chosen pivoted position of the jointed elements by means of a tightening element, wherein each jointed element comprises on one end a ball joint and at the opposite end a socket joint to receive a ball joint, and wherein each jointed element is constructed in two parts in the length direction, whereby the two parts can be adjusted against one another for locking purposes, and wherein the two parts of each jointed element are pivotable against each other about a common joint axis in such a way that by causing the socket joint of a jointed element to open, the ball joint of the same jointed element is also caused to open.

2. The tightening device of claim 1, wherein the two parts of the jointed elements are z-shaped in construction when viewed from the side so that with one of the two parts the upper part of the ball joint is connected with the lower part of the socket joint and with the other of the two parts the lower part of the ball joint is connected to the upper part of the socket joint.

3. The tightening device of claim 2, wherein the joint axis is disposed in the middle of the jointed element and in a plane of a length cut through the ball joint and the socket joint, such that the ball joint and the socket joint can be opened to an angle of aperture between the two parts.

4. The tightening device of claim 3, wherein the angle of aperture from the proximal jointed element to the distal jointed element from jointed element to jointed element is represented by $\alpha_{prox}>\alpha_n>\alpha_{n+1}> \ldots >\alpha_{dist}\cong 0$.

5. The tightening device of claim 4, wherein at right angles to the length cut of the ball joint through the sphere equator of the ball joint of each jointed element is constructed a through bore, into which for each of the two parts of the ball joint a pin projecting from the exterior over the surface of the ball joint is arranged, which is guided in a groove constructed in the socket joint to guide and to limit an angle of pivot of the individual jointed elements against one another in the state when connected with another jointed element.

6. The tightening device of claim 5, wherein a handle acting as a tightening element can be locked to the jointed element at the proximal end of the arm for the adjustment and locking of the jointed elements.

7. The tightening device of claim 6, wherein a tool can be affixed to the jointed element at the distal end of the arm.

8. A flexible tightening device having an arm comprising several jointed elements moveable against one another, in which the arm may be locked in a chosen pivoted position of the jointed elements by means of a tightening element, wherein each jointed element comprises on one end a ball joint and at the opposite end a socket joint to receive a ball joint, wherein each jointed element is constructed in two parts in the length direction, whereby the two parts can be adjusted against one another for locking purposes, and wherein the two parts of the jointed elements are z-shaped in construction when viewed from the side so that with one of the two parts the upper part of the ball joint is connected with the lower part of the socket joint and with the other of the two parts the lower part of the ball joint is connected to the upper part of the socket joint.

* * * * *